(12) United States Patent  (10) Patent No.: US 7,172,796 B2
Kinoshita et al.  (45) Date of Patent: Feb. 6, 2007

(54) BALLOON CATHETER

(75) Inventors: Yasushi Kinoshita, Shizuoka (JP); Hiraku Murayama, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 168 days.

(21) Appl. No.: 10/632,952

(22) Filed: Aug. 4, 2003

(65) Prior Publication Data
US 2004/0101644 A1 May 27, 2004

(30) Foreign Application Priority Data
Aug. 5, 2002 (JP) ............................. 2002-226923

(51) Int. Cl.
B29D 22/00 (2006.01)
B29D 23/00 (2006.01)
B32B 1/08 (2006.01)
(52) U.S. Cl. .................. 428/36.3; 428/36.1; 428/35.2; 604/96.01; 604/103.06; 604/103.09; 606/194
(58) Field of Classification Search ............... 428/35.7, 428/36.1, 35.2, 36.3; 604/96.01, 103.06, 604/103.09; 606/194
See application file for complete search history.

(56) References Cited

U.S. PATENT DOCUMENTS 5,868,704 A 2/1999 Campbell et al.
6,303,697 B1 10/2001 Yuan et al.

2001/0043998 A1 11/2001 Chen et al.
2002/0081404 A1 6/2002 Schaible et al.
2003/0093107 A1 5/2003 Parsonage et al.

FOREIGN PATENT DOCUMENTS

WO WO 95/18647 7/1995
WO WO 98/05377 2/1998
WO WO 01/34062 A2 5/2001

Primary Examiner—Michael Miggins
(74) Attorney, Agent, or Firm—Buchanan Ingersoll PC

(57) ABSTRACT

A balloon catheter includes a long-sized body extending between a proximal end and a distal end, the body internally having at least one lumen, and a balloon made from a composite material composed of short-fibers for reienforcement and a matrix resin, the balloon being disposed on the distal side of the long-sized body. The short-fibers are oriented in the balloon in such a manner that in a longitudinal cross-section of the balloon, 25% or more of the short-fibers are oriented in the major-axis direction of the balloon, 25% or more of the short-fibers are oriented in the direction oblique to the major-axis direction, and the remaining short-fibers are oriented in the direction nearly perpendicular to the major-axis direction; and in a diametrical cross-section of the balloon, 8% or more of the short-fibers are oriented in the circumferential direction of the balloon, 25% or more of the short-fibers are oriented in the direction perpendicular to the circumferential direction, that is, in the major-axis direction, and the remaining short-fibers are oriented in the direction oblique to the circumferential direction. The balloon catheter exhibits a high strength to withstand pressure and a good trackability.

11 Claims, 5 Drawing Sheets

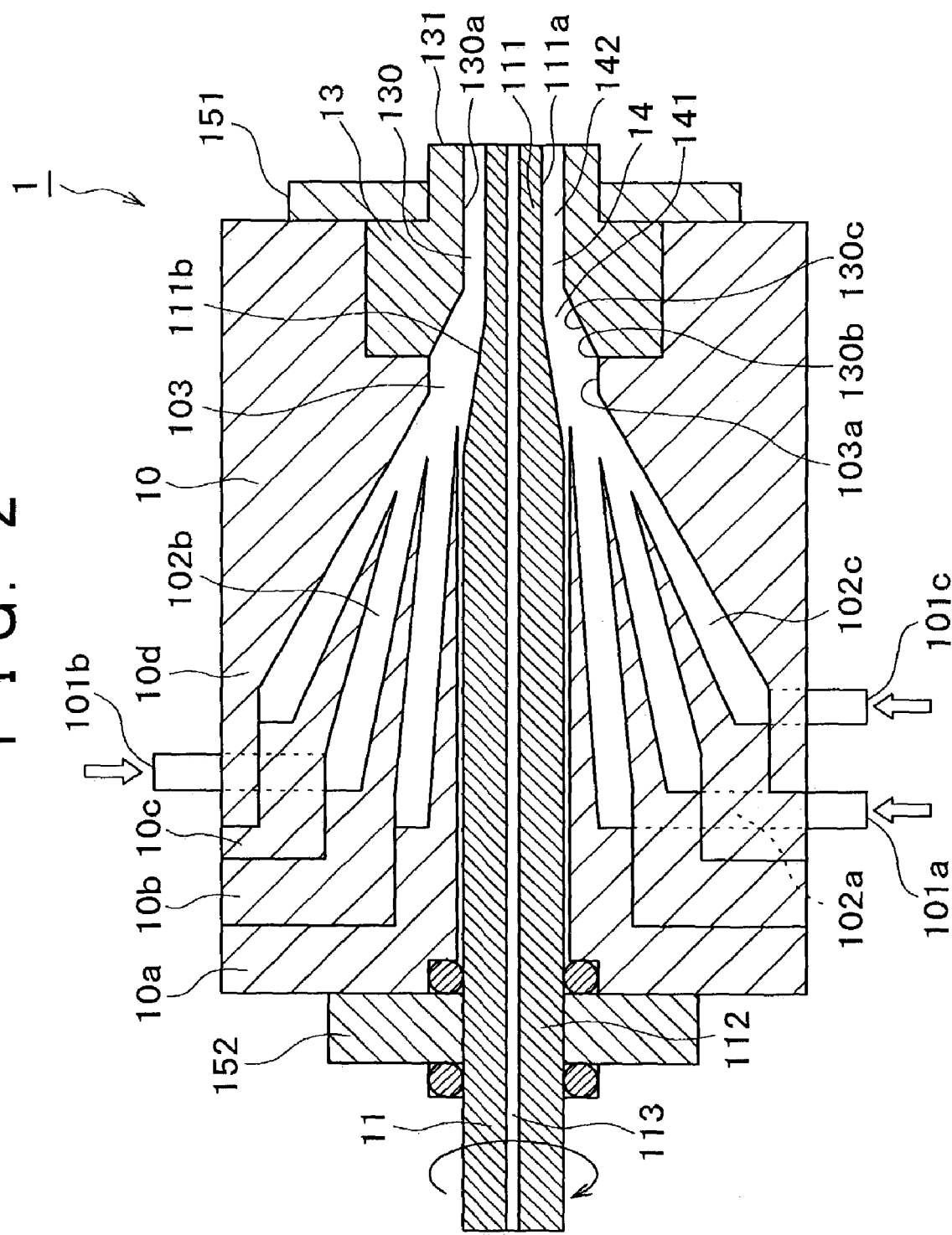

DIRECTION
OF GRAVITY

BALLOON CATHETER

BACKGROUND OF THE INVENTION

The present invention relates to a balloon catheter for medical application, and particularly to a dilation balloon catheter to be inserted in a body cavity such as a blood vessel, which catheter has a dilation balloon to be very easily insertable in a narrow, eccentric or meandering stenosis portion, or a branch portion in the body cavity in order to dilate the stenosis portion.

A dilation balloon catheter generally includes inner and outer tubes to be inserted in a body cavity and a cylindrical balloon connected to the inner and outer tubes.

Such a cylindrical balloon has been required to satisfy inconsistent needs for a sufficient strength to withstand a pressure for dilation of the balloon and a good trackability in a blood vessel. Specifically, the dilation balloon has been required to have a characteristic easily insertable even in a very narrow, eccentric, or meandering stenosis portion without damaging the stenosis portion while keeping a high strength to withstand pressure.

To meet these requirements, various balloons made from polymers have been proposed.

Balloon catheters made from thermoplastic polymers have been known. Examples of the thermoplastic polymers used for such balloon catheters include an ethylene-butylene-styrene block copolymer containing polyethylene, ionomer, and low molecular weight polystyrene, and further polypropylene (if needed); a derivative from the above copolymer by substituting ethylene and butylenes by butadiene or isoprene; polyvinyl chloride; polyurethane; polyester or copolyester; polyamide or polyamide elastomer; thermoplastic rubber; silicone-polycarbonate copolymer; and ethylene-vinyl acetate copolymer.

A balloon made from thermoplastic polyimide has been also proposed, for example, in Published Japanese Translation of a PCT Application No. Hei 9-507148 (WO95/18647).

However, in recent years, a balloon catheter including a balloon having a higher strength to withstand a pressure has been required.

It has been also known to use a composite material obtained by combining a resin with long-fibers (filaments) or a fiber-structure such as a woven fabric or knit fabric of the long-fibers for enhancing the strength to withstand pressure of a balloon.

For example, Published Japanese Translation of a PCT Application No. 2001-504359 (WO98/05377) has proposed a composite material used for a balloon, wherein the composite material is obtained by forming a resin integrally with long-fibers in the form of yarns or a fiber-structure such as a plain weave fabric, satin fabric, twilled fabric, basket weave fabric, braid, or winding fabric of the long-fibers. The composite material obtained by forming a resin integrally with such long-fibers or a fiber-structure of the long-fibers, however, has a disadvantage that it is generally difficult to sufficiently impregnate a gap between the adjacent single fibers in the yarn with the resin, to cause defects not impregnated with the resin. In particular, in the case of using multi-filaments, such detects not impregnated with a resin are liable to occur. Another disadvantage is that since the method disclosed in the above document requires the step of forming the fiber-structure into the shape of a balloon, if it is intended to produce a balloon having a fine diameter, the uniformity of production and the production yield may be degraded.

U.S. Ser. No. 2001/43998 has disclosed a balloon catheter including a balloon reinforced by reinforcing bodies in the form of short-fibers disposed in a matrix resin. According to the method disclosed in this document, a reinforcing resin such as total aromatic polyester forming liquid crystal in a melted state is disposed in the form of whiskers (pulp) in a matrix resin by blending the reinforcing resin with the matrix resin and simultaneously melting the reinforcing resin together with the matrix resin in an extrusion cylinder, extruding the compound from discharge nozzles of a die, to form the melted reinforcing resin into whisker-like shapes elongated in the extrusion direction by shearing orientation caused at the time of extrusion from the discharge nozzles, and solidifying the extruded product by cooling in a water bath, wherein the reinforcing resin in the form of particles before melting is disposed in the form of whiskers (pulp) in the matrix resin by shearing applied to the melted reinforcing resin. The above document has also disclosed that the reinforcing resin can be disposed in the form of whiskers by increasing the draft ratio of general extrusion molding, and further the reinforcing resin can be disposed in the form of whiskers oriented in the circumferential direction of the tubular parison to be molded into the balloon by rotating a mandrel (core) or an outer die portion of the extrusion die.

The extrusion method disclosed in the above-described document, however, has a disadvantage that since the reinforcing resin is disposed in the form of whiskers (pulp) in the matrix resin by discharging the reinforcing resin from a specific number of the discharge nozzles of the die while applying a rotational force and a shearing force to the reinforcing resin, the reinforcing resin is formed into the whiskers (pulp) extending in lines of the number corresponding to that of the discharge nozzles of the die, and accordingly, the reinforcing resin is not present among the lines of the whiskers, with a result that the reinforcing effect becomes insufficient, to simply cause pin-holes and cracks. Further, as is easily appreciated by those skilled in the art, it often fails to obtain a sufficient reinforcing effect only by discharging the melted reinforcing resin. On the other hand, it may be conceivable to improve the crystallinity of the reinforcing resin by a heat-treatment; however, such a heat-treatment must be performed at a temperature being too high to deteriorate or thermally deform the matrix resin. It may be also conceivable to use a liquid crystal resin having a chemical structure allowing the resin to be molded or crystallized at a low temperature against which the matrix resin withstands; however, such a liquid crystal resin is poor in rigidity as the reinforcing material.

SUMMARY OF THE INVENTION

A need exists for a balloon catheter for medical application, which catheter includes a highly reinforced balloon.

A further need exists for a balloon for medical application, which balloon has a high withstand pressure and a good trackability allowing the balloon to easily reach even in a terminal blood vessel, and a balloon catheter including such a balloon.

According to one aspect of the present invention, there is provided a balloon catheter including a long-sized body extending between a proximal end and a distal end, the body internally having at least one lumen, and a balloon made from a composite material composed of short-fibers for reinforcement and a matrix resin, the balloon being disposed on the distal side of the long-sized body. The short-fibers are oriented in the balloon in such a manner that in a longitudinal cross-section of the balloon, 25% or more of the short-fibers are oriented in the major-axis direction of the balloon, 25% or more of the short-fibers are oriented in the direction oblique to the major-axis direction, and the remaining short-fibers are oriented in the direction nearly perpendicular to the major-axis direction; and in a diametrical cross-section of the balloon, 8% or more of the short-fibers are oriented in the circumferential direction of the balloon, 25% or more of the short-fibers are oriented in the direction perpendicular to the circumferential direction, that is, in the major-axis direction, and the remaining short-fibers are oriented in the direction oblique to the circumferential direction.

The short-fiber is preferably at least one kind selected from a group consisting of organic short-fibers and inorganic short-fibers.

The organic short-fiber is preferably a polymer short-fiber.

The inorganic short-fiber is preferably at least one kind selected from a group consisting of carbon short-fibers and metal short-fibers.

The carbon short-fiber is preferably made from nanocarbon.

The short-fiber is preferably one kind selected from a group consisting of nanocarbon tubes and nanocarbon fibers.

The metal short-fiber is preferably a whisker.

The composite material is preferably a material in which the short-fibers are uniformly dispersed in the matrix resin.

The short-fibers are preferably subjected to a surface modifying treatment.

The composite material is preferably a material in which the short-fibers are dispersed in the matrix resin by blending the short-fibers in the matrix resin while applying ultrasonic vibration to the short-fibers and the matrix resin.

The composite material is preferably obtained by blending the short-fibers in a precursor of the matrix resin before polymerization reaction, or in the precursor being during polymerization and thereby having a viscosity lower than a viscosity of the final polymerized product as the matrix resin.

In this specification, the state in which the short-fibers are uniformly dispersed in the matrix resin is evaluated as follows: namely, the number "n" of the short-fibers per unit area is measured on the basis of a scanning electron microscopic photograph at each of 30 points on a longitudinal cross-section or a circumferential cross-section of the molded balloon and an average value (x) and a population variance ($\sigma$) are calculated, and if the number "m" of the short-fibers per unit area is within a range of $x \pm 3\sigma$, it is determined that the short-fibers are uniformly dispersed in the matrix resin.

As described above, the balloon catheter of the present invention has the balloon made from a composite material composed of short-fibers for reinforcement and a matrix resin, wherein the short-fibers are disposed not in lines in the balloon and are nearly uniformly dispersed in the balloon.

Accordingly, since the entire balloon is reinforced with the short-fibers, the strength of the entire balloon is improved. As a result, it is possible to provide a balloon capable of reducing occurrence of pin-holes and cracks and enhancing the withstand pressure, and to provide a balloon catheter including such a balloon. Also, since the flexibility of the balloon can be sufficiently kept, it is possible to provide a balloon excellent in trackability in a blood vessel, and to provide a balloon catheter including such a balloon.

In the case of subjecting the short-fibers to a surface modifying treatment for improving adhesion with the matrix resin, it is possible to sufficiently impregnate gaps among the short-fibers with the matrix resin, and hence to enhance the balloon reinforcing effect.

In particular, in the case of using a composite material obtained by dispersing the high modulus short-fibers in the matrix resin by applying ultrasonic vibration to the matrix resin and the short-fibers, since the short-fibers are uniformly dispersed in the matrix resin, it is possible to further enhance the reinforcing effect over the entire balloon, and hence to further improve the strength of the balloon.

BRIEF DESCRIPTION OF THE DRAWINGS

These and other objects, features, and advantages of the present invention will become more apparent from the following detailed description in conjunction with the accompanying drawings, wherein:

FIGS. 1A and 1B show one orientation example of short-fibers in a balloon of a balloon catheter of the present invention, wherein FIG. 1A is a photograph of a longitudinal cross-section of the balloon along the major-axis direction (longitudinal axis direction), which is taken at a magnification of 5,000 times by a field emission type scanning electron microscope, and FIG. 1B is a photograph of a diametrical cross-section of the balloon along the circumferential direction, which is taken as a magnification of 5,000 times by the same electron microscope;

FIG. 2 is a schematic sectional view showing one example of a co-extrusion die for producing a laminated tubular body according to the present invention;

DETAILED DESCRIPTION OF THE PREFERRED EMBODIMENTS

Hereinafter, preferred embodiments of the present invention will be described in detail with reference to the drawings.

A balloon catheter having one or a plurality of lumens and a balloon positioned at its distal end is used for an angioplasty for dilating and opening a stenosis portion formed in a vessel system.

Figure 1B:
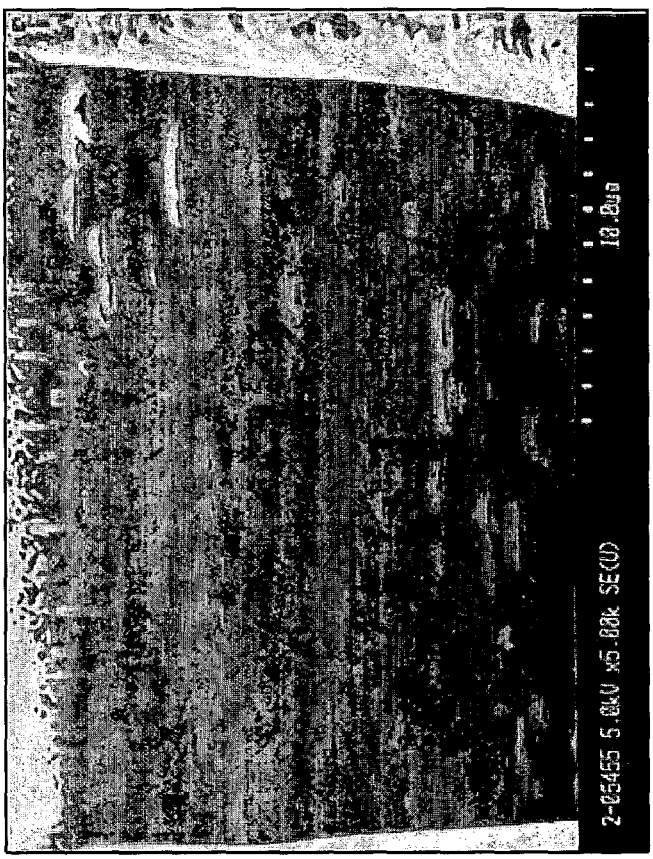
Figure 1A:
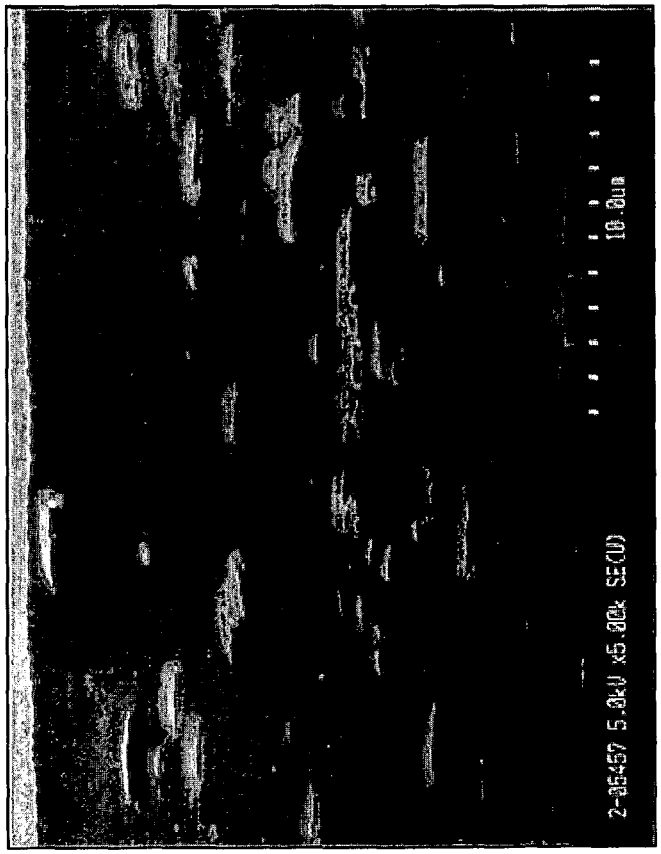
Figure 3:
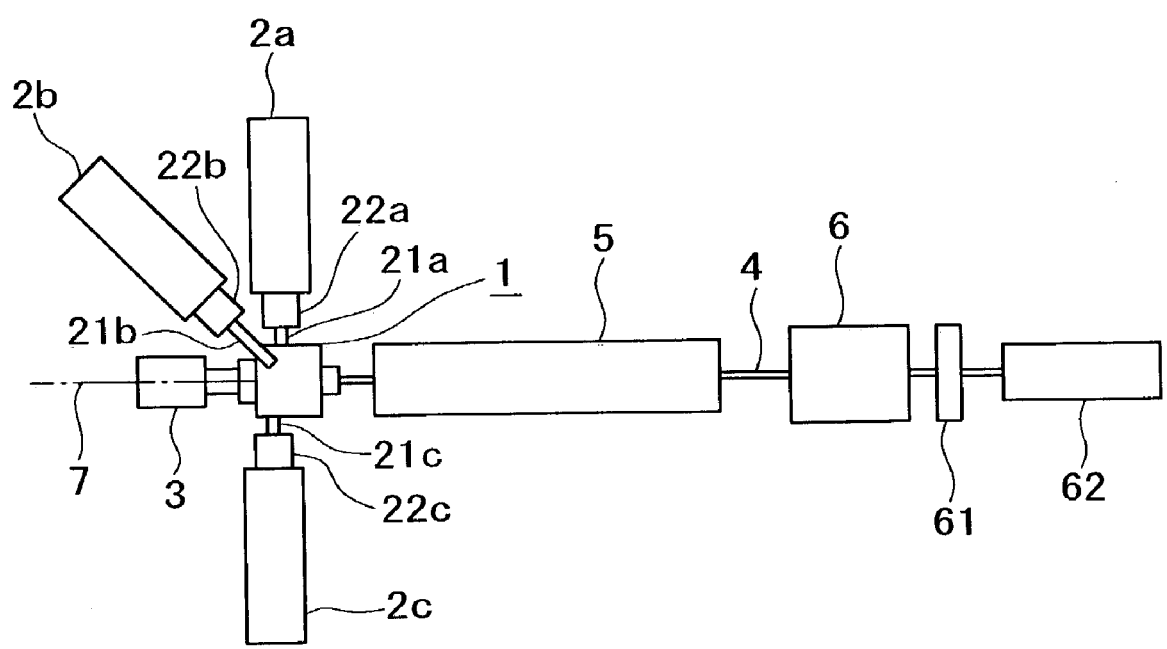
FIG. 3 is a typical view showing one example of an extrusion line for producing a laminated tubular body, which line includes the co-extrusion die according to the present invention.
Figure 4:
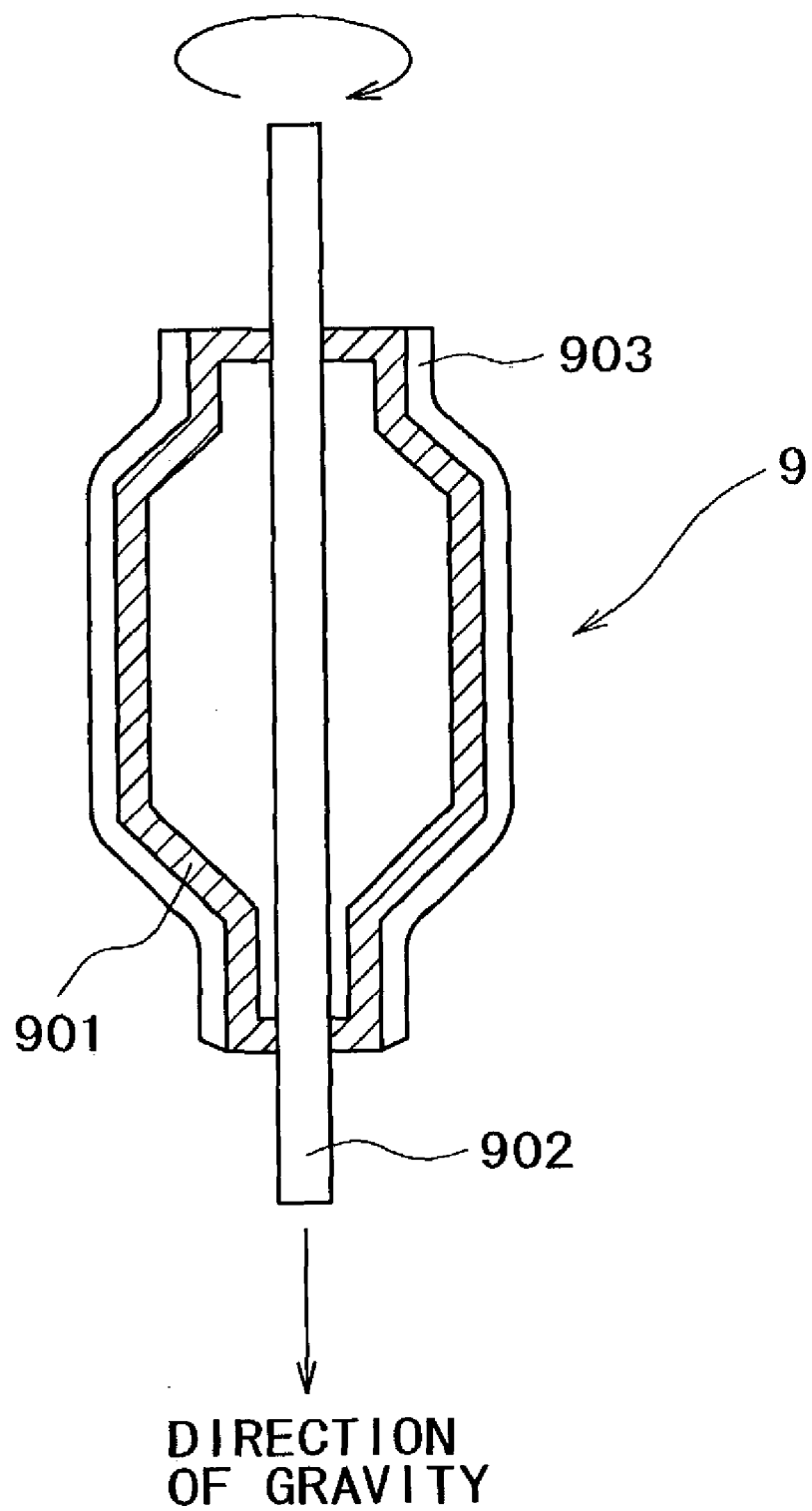
FIG. 4 is a view showing one example of a balloon producing apparatus according to the present invention.
Figure 5:
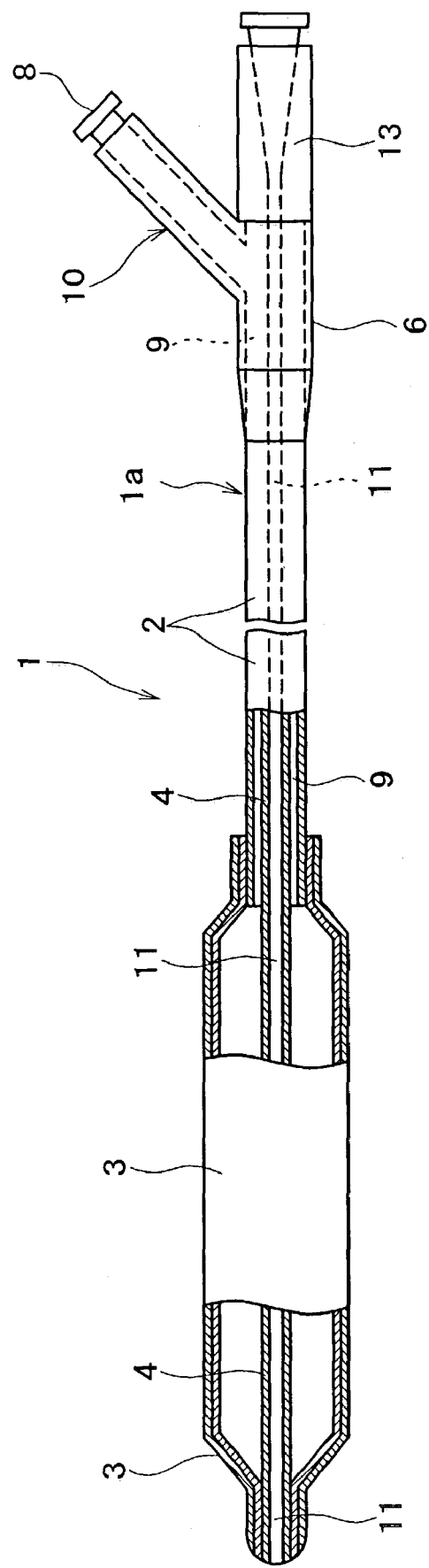
FIG. 5 is a sectional view showing one example of the balloon catheter of the present invention.

FIGS. 1A and 1B show one orientation example of short-fibers in a balloon of a balloon catheter of the present invention, wherein FIG. 1A is a photograph of a longitudinal cross-section of the balloon along the major axis direction, which is taken at a magnification of 5,000 times by a field emission type scanning-electron microscope (FE-SEM) (Model S-4700, commercially available from Hitachi, Ltd.), and FIG. 1B is a photograph of a diametrical cross-section of the balloon along the circumferential direction, which is taken as a magnification of 5,000 times by the same FE-SEM. FIG. 2 is a schematic sectional view showing one example of a co-extrusion die for a laminated tubular body according to the present invention. FIG. 3 is a typical view showing one example of an extrusion line for a laminated tubular body, which line includes the co-extrusion die according to the present invention. FIG. 4 is a view showing one example of a balloon producing apparatus according to the present invention. FIG. 5 is a sectional view showing one example of the balloon catheter of the present invention.

FIG. 5 shows one example of the balloon catheter of the present invention, which includes a balloon made from a composite material of the present invention (to be described later). The balloon catheter shown in FIG. 5 includes a long-sized body 1a and a balloon 3. The long-sezed (elongated) body 1a comprises an inner tube 4 and an outer tube 2. The balloon is disposed on the distal side of the long-sized body 1a. The inner tube 4 has an inner lumen 11 opened at the distal end of the inner tube 4. The outer tube 2, provided coaxially with the inner tube 4, has a distal end on the proximal side from the distal end of the inner tube 4 by a specific length. The balloon 3 is fixed to both a distal end portion of the inner tube 4 and a distal end portion of the outer tube 2. The inner volume of the balloon 3 is dilatable or deflatable by injecting or removing a drive fluid in or from the balloon 3. The inner tube 4 is made from a superelastic metal. The balloon catheter further includes a branch hub 10 having an outer tube hub 6 and an inner tube hub 13. The outer tube hub 6 is air-tightly or liquid-tightly fixed to a proximal end portion of the outer tube 2, and has an opening portion 8 communicated to a lumen 9 of the outer tube 2. The opening portion 8 functions as an inlet or outlet through which the drive fluid is to flow in or from the balloon 3 for dilating or deflating the balloon 3.

The balloon of the balloon catheter of the present invention is made from a composite material composed of a matrix resin and reinforcing short-fibers.

In the longitudinal cross-section of the balloon, 25% or more of the short-fibers are oriented in the major-axis direction, 25% or more of the short-fibers are oriented in the direction oblique to the major-axis direction, and the remaining short-fibers are oriented in the direction nearly perpendicular to the major-axis direction.

In the diametrical cross-section of the balloon, 8% or more of the short-fibers are oriented in the circumferential direction, 25% or more of the short-fibers are oriented in the direction perpendicular to the circumferential direction, that is, in the major-axis direction, and the remaining short-fibers are oriented in the direction oblique to the major-axis direction.

In this way, the short-fibers are disposed over the entire balloon in such a manner as not to be in order but to be oriented at the above-described specific orientation ratio. Accordingly, any specific weak portion is not formed in the balloon, and at any portion of the balloon, the matrix resin is sufficiently reinforced with the short-fibers. As a result, the balloon has a high strength to withstand pressure and thereby a high resistance against pin-holes and cracks at the time of dilation of the balloon.

FIGS. 1A and 1B show one orientation example of the short-fibers in the balloon, wherein FIG. 1A shows a longitudinal cross-section of the balloon along the major-axis direction taken at a magnification of 5,000 times by the FE-SEM, and FIG. 1B shows a diametrical cross-section of the balloon along the circumferential direction taken at a magnification of 5,000 times by the FE-SEM.

The length of each of the reinforcing short-fibers is not particularly limited, but from the viewpoint of allowing sufficient impregnation of the matrix resin in each gap between adjacent short-fibers, the length of each of the short-fibers is preferably, 5 mm or less, more preferably, 3 mm or less, most preferably, 1 mm or less. The aspect ratio (ratio of the length to the diameter) of each short-fiber is not particularly limited, but from the viewpoint of ensuring a sufficient reinforcing effect, the aspect ratio is preferably in a range of 10 or more, more preferably, 30 or more, most preferably, 100 or more.

The content of the reinforcing short-fibers is in a range of 10 wt % or more and 25 wt % or less on the basis of the total weight of the composite material.

The orientations of the short-fibers in the balloon of the present invention, as seen in the longitudinal cross-section along the major-axis direction and the diametrical cross-section along the circumferential direction, are as follows:

In the longitudinal cross-section, 25% or more, more preferably, 25 to 55% of the short-fibers are oriented in a first orientation parallel to the major-axis direction (longitudinal axis direction), and 25% or more, more preferably, 25 to 55% of the short-fibers are oriented in a second orientation oblique to the major-axis direction. The term "orientation oblique to the major axis direction" used herein means the orientation oblique to the major-axis direction by an angle of ±20 to 70°.

In the diametrical cross-section, 8% or more, preferably, 8 to 20% of the short-fibers are oriented in a first orientation parallel to the circumferential direction, and 25% or more, preferably, 25 to 55% of the short-fibers are oriented in a second orientation perpendicular to the circumferential direction.

With this configuration, the reinforcing short-fibers are oriented in the longitudinal, circumferential, and oblique directions, to thereby improve the hoop strength and the longitudinal strength (strength in the major-axis direction) of the balloon.

The short-fibers used for reinforcing the balloon of the present invention are generally classified into organic short-fibers (1), inorganic short-fibers (2), metal short-fibers (included in the inorganic fibers) (3), and other inorganic short-fibers (4).

Examples of the organic fibers (1) include polymer short-fibers, for example, short-fibers of liquid crystal polyester such as poly-p-hydroxybenzoate copolymer, which fibers are commercially available in the trade names of "EKONOL", "VECTRA", "XYDAR", and "NOVACCURATE"; aramid short-fibers, such as, short-fibers of poly-p-phenylene terephthalamide or a copolymer thereof, or pulp of the aramid fibers, which fibers are commercially available in the trade names of "KEVLAR", "ARENKA", and "TECHNORA"; short-fibers of a total aromatic polymer such as poly-p-phenylene benzobisoxazole, poly-p-phenylene benzobisthiazole, or a copolymer thereof; short-fibers of high modulus polyethylene, which fibers are commercially available in the trade names of "TECHMILON", "DYNEEMA", and "SPECTRA"; short-fibers of polyoxymethylene (polyacetal) and whiskers thereof, which fibers are commercially available in the trade name of "TENAC SD"; and short-fibers of polyvinyl alcohol.

Examples of the inorganic fibers (2) include carbon short-fibers, carbon whiskers, and nanocarbon based tubes, horns, and fibers.

Examples of the metal short-fibers (3) include boron short-fibers, titanium alloy short-fibers, steel short-fibers, and aluminum alloy short-fibers.

Examples of the other inorganic short-fibers (4) include potassium titanate short-fibers, silicon carbide (SiC) short-fibers and whiskers thereof, alumina short-fibers, and glass fibers.

Nanocarbon is a new carbon material following graphite, diamond, and fullerene. The nanocarbon is a generic name of a nanosize structure formed by carbon atoms bonded to each other in a spherical or cylindrical shape. Examples of kinds of the nanocarbon include a single layer carbon nanotube (diameter: about 1 nm) having only one cylindrical structure of carbon atoms, a carbon nanohorn (diameter: about 1 nm to several nm), a multi-layer carbon nanotube (diameter: several nm to several tens nm) having a stack of cylindrical structures of carbon atoms; and a carbon nanofiber (diameter: several tens nm to several hundreds nm; and length: several tens μm). In particular, the carbon nanofiber has an aspect ratio of 10 to 800 or more, which is sufficient for reinforcing fibers.

The study for synthesis of such nanocarbon on a large scale has been made by the carbon based high function material technical project of Ministry of Economy, Trade, and Industry. The nanocarbon products obtained by test apparatus in the project are commercially available.

Among the above-described kinds of the nanocarbon, the carbon nanotubes or carbon nanofibers are preferably used as the short-fibers according to the present invention.

The matrix resin may be a thermoplastic resin as a general plastic having a certain level of flexibility, or a thermosetting or cross-linking resin such as rubber.

Examples of the thermoplastic resins include a polyester such as polyethylene terephthalate or polybutylene terephthalate, and a polyester elastomer using a polyester as a hard segment; a polyolefin such as polyethylene or polypropylene, a polyolefin elastomer, and a copolymer polyolefin using a metallocene catalyst; a vinyl based polymer such as polyvinyl chloride, PVDC, or PVDF; polyamide including nylon and a polyamide elastomer (PAE); and other thermoplastic resins such as polyimide, polystyrene, SEBS resin, polyurethane, a polyurethane elastomer, ABS resin, acrylic resin, polyarylate, polycarbonate, polyoxymethylene (POM), polyvinyl alcohol (PVA), fluorocarbon resin (ETFE, PFA, PTFE), saponification of ethylene-vinyl acetate, (ethylene-polyvinyl alcohol) copolymer, ethylene vinyl acetate, carboxymethyl cellulose, methyl cellulose, cellulose acetate, vinyl polysulfone, a liquid crystal polymer (LCP), polyether sulfone (PES), polyether ether ketone (PEEK), polyphenylene oxide (PPO), and polyphenylene sulfide (PPS). Polymer derivatives of these thermoplastic resins may be used.

Examples of the thermosetting or cross-linking resins include vulcanization rubber, silicone resin, epoxy resin, and two-liquid reaction type polyurethane resin.

Polymer alloys containing either of the above-described thermoplastic resins and thermosetting or cross-linking resins may be also used.

In addition, the resin may be used in the form of a resin solution formed by dissolving the resin in a solvent.

To improve the adhesion of the short-fibers to the matrix resin, it is preferred to physically, physicochemically, and/or chemically modify the surfaces of the short-fibers. Typical examples of the surface treatments (surface modifying treatments) include a surface treatment by a silane coupling agent and a surface treatment using a titanium coupling agent, which are generally used for glass fibers.

In addition to the above-described two kinds of coupling agents, the following various kinds of surface-treatment agents may be used singly or in combination for improving the adhesion, that is, adhesive strength of the surfaces of the short-fibers with the matrix resin:

(1) higher fatty acid: stearic acid or oleic acid;
(2) higher fatty acid ester or higher fatty acid amid;
(3) metal salt of higher fatty acid: calcium stearate, magnesium stearate, or zinc stearate;
(4) higher alcohol;
(5) wax; low molecular weight polyethylene wax or low molecular weight polypropylene wax; and
(6) polar polyolefin: polyolefin grafted with maleic acid anhydride, acid-propylene copolymer, or chlorosulfonated polyolefin.

These surface modifying agents may be used in accordance with a manner that the surfaces of the short-fibers be treated by the surface modifying agents and then the short-fibers be dispersed in the matrix resin, or in a manner that the surface modifying agents be added simultaneously in compounding the short-fibers with the matrix resin. It is appreciated to a person skilled in the art that depending on the combination of the reinforcing short-fibers and the matrix resin, the surface modifying agents effective for the short-fibers can be selected.

A method of preparing a composite material composed of the matrix resin and the short-fibers nearly uniformly dispersed therein according to the present invention will be described below.

If the matrix resin is a meltable thermoplastic resin, a suitable one of known compounding (kneading) methods can be selected. Examples of kneaders include a single or twin screw type kneader, a rubber roll type kneader, and a mill stone type kneader.

Recently, in-situ polymerization (kneading upon polymerization) has been advantageously used for compounding reinforcing fibers with a matrix resin, particularly, for compounding micro-sized reinforcing fibers such as nanocarbon based tubes, horns, or fibers with a matrix resin.

One example of the in-situ polymerization involves dispersing the reinforcing short-fibers in the matrix resin before polymerization of the matrix resin or in a state that the viscosity of the matrix resin (or a monomer as a precursor, a base resin/curing agent of a thermosetting agent) is low during polymerization, thereby significantly improving the dispersibility of the short-fibers. Such a method is particularly effective for a combination of short-fibers and a matrix resin, which composition makes it difficult to obtain a sufficient dispersibility of the short-fibers in the matrix resin by the method of kneading the short-fibers in the melted matrix resin.

To improve the dispersibility of the reinforcing short-fibers in the matrix resin, it is preferred to use the following ultrasonic vibration technique. According to the ultrasonic vibration technique, in the step of compounding the short-fibers with the matrix resin, ultrasonic vibration is applied to the compound for a specific time, to disentangle or loosen the short-fibers partially aggregated, thereby allowing the matrix resin to permeate in the short-fibers.

Such a ultrasonic vibration technique may be combined with the method of compounding the short-fibers with the matrix resin in a melted state; however, a preferred method using the ultrasonic vibration technique involves dissolving the matrix resin in a suitable solvent, blending the short-fibers in the resin solution, and applying ultrasonic vibration to the resin solution (using a stirring blade if needed), thereby allowing the resin solution to dispersibly permeate in the short-fibers.

If the matrix resin is produced by solution polymerization, before, during, or after polymerization, the short-fibers may be blended with the precursor of the matrix resin or the polymerized matrix resin, followed by applying ultrasonic vibration thereto.

The use of the compounding method described above makes it possible to obtain a composite material in which the reinforcing short-fibers are nearly uniformly dispersed in the matrix resin. The nearly uniform dispersion of the short-fibers in the matrix resin is advantageous in improving the adhesive strength of the interface between each of the short-fibers and the matrix resin, thereby enhancing the effect of reinforcing the balloon with the short-fibers.

In the case of using the matrix resin solution, the step of dispersing the reinforcing short-fibers in the matrix resin solution is followed by the subsequent steps, for example, removal of the solvent, cleaning, drying, and pelletization in accordance with a known process, to obtain resin pellets or powders of a composite material in which the short-fibers are desirably dispersed in the matrix resin.

<Formation of Tubular Parison by Molding>

If the matrix resin is a thermoplastic resin, a tubular parison to be molded into the balloon can be produced by preparing resin pellets or powders of a composite material including the matrix resin and the short-fibers dispersed therein as described above, and molding the composite material into the parison by a known extrusion molding process or a rotational extrusion molding process described below. A tubular parison in which the short-fibers are oriented in the longitudinal direction can be produced by drawing the composite material in the major-axis direction upon extrusion. On the other hand, a tubular parison in which the short-fibers are oriented both in the circumferential and longitudinal directions can be produced by the rotational extrusion molding process. The resultant tubular parison is then subjected to biaxial orientation blow molding, to thus produce the balloon of the present invention.

The balloon used for the balloon catheter of the present invention is produced by selecting one of the above-described molding methods depending on the kinds of the matrix resin and the short-fibers, wherein the orientations of the short-fibers in the balloon are specified in such a manner that in the longitudinal cross-section of the balloon, 25% or more of the short-fibers are oriented in the major-axis direction, 25% or more of the short-fibers are oriented in the direction oblique to the major-axis direction, and the remaining short-fibers are oriented in the direction nearly perpendicular to the major-axis direction; and in the diametrical cross-section of the balloon, 8% or more of the sort-fibers are oriented in the circumferential direction, 25% or more of the short-fibers are oriented in the direction perpendicular to the circumferential direction, that is, in the major-axis direction, and the remaining short-fibers are oriented in the direction oblique to the circumferential direction.

FIG. 2 is a schematic sectional view of a three-layer lamination type co-extrusion die 1 used for producing a laminated tubular body according to the present invention.

The extrusion die 1 used for the present invention is adapted to form a tubular body by co-extruding multi-layered materials. In the following description, the left side (or lower side) of the figure is taken as the upstream side (proximal side) of the extruding direction, and the right side (or upper side) of the figure, that is, the direction along which the multi-layered materials are extruded is taken as the downstream side (distal side) of the extruding direction. The extrusion die 1, which is configured as a rotary circular die, includes a die body 10, a mandrel 11, and a die 13. The mandrel 11 passes through the die body 10. The die 13 is disposed at the distal end of the die body 10 on the downstream side of the extruding direction in such a manner as to be concentric with the mandrel 11. In this extrusion die 1, at least one of the mandrel 11 and the die 13 is configured as rotatable around an axis extending in the extruding direction.

The following description will be made mainly by example of a type in which only the mandrel 11 is rotatable, although either or both of the mandrel 11 and the die 13 may be rotatable. The type in which only the mandrel 11 is rotatable is hereinafter referred to as "rotary point type".

The die body 10 shown in FIG. 2 includes a polymer flow line having a manifold structure described below. To be more specific, the die body 10 includes polymer inlets 101a to 101c, a single merge portion 103 on the downstream side of the extruding direction, and tubular branch passages 102a to 102c. The tubular branch passages 102a to 102c extend in annular shapes from the polymer inlets 101a to 101c, and are gradually diametrically reduced and are independently communicated to the merge portion 103, to merge at the merge point 103. The die body 10 internally including such a manifold structure can be built up by assembling a plurality of members 10a to 10d into one body.

The mandrel 11 has a hollow structure defining an inner gap 113 extending in the axial direction. The mandrel 11 has a polymer contact portion (hereinafter, referred sometimes to as "rotary point") 111 having a cylindrical outer peripheral surface 111a projecting from the merge point 103 on the downstream side (distal side) of the extruding direction.

A shaft portion 112, excluding the rotary point 111, of the mandrel 11 passes through the die body 10, which shaft portion 112 is connected to a drive portion 3 (see FIG. 3) for rotating the mandrel 11. The shaft portion 112 is configured as not in contact with the polymer flow.

The die 13 internally has a cylindrical space 130 defined by an inner peripheral surface 130a having a diameter larger than that of the outer peripheral surface 111a of the mandrel 11. At least an upstream end 130b of the cylindrical space 130 in the extruding direction has the same diameter as that of an end 103a of the merge portion 103 of the die body 10 and is continuous to the end 103a of the merge portion 103.

A flow passage 14 of merged polymers is formed in the cylindrical space 130 of the die 13 in such a manner as to be surrounded by the outer peripheral surface 111a of the rotary point 111 of the mandrel 11 and the inner peripheral surface 130a of the die 13. The flow passage 14, which is often called "polymer merge passage", is thus formed between the die 13 and the rotary point 111 of the circular die 1.

The flow passage 14 in the die 13 preferably further includes a taper flow passage 141 with its diameter gradually reduced. The taper flow passage 14 is continuous to the merge portion 103 at which the branch passages 102a to 102c merge while being gradually, diametrically reduced.

Concretely, the outer peripheral surface 111a of the mandrel 11 and/or the inner peripheral surface 130a of the die 13 are gradually diametrically reduced in the downstream direction from the merge portion 103 of the die body 10, to form a mandrel taper portion 111b and/or a die taper portion 130c, thereby forming the taper flow passage 141 with its cross-section gradually reduced. An extrusion flow passage 142 is preferably provided so as to be continuous to the downstream end of the taper flow passage 141. The diameter of the extrusion flow passage 142 is nearly equal to that of a mouthpiece 131. In other words, the extrusion flow passage 142 has a shape and a size close to those of a final tubular body.

The mouthpiece 131 of the die 13 is fixed to the die body 1 by means of a die holder 151.

The shaft 112 of the mandrel 11 is held on the other end of the die body 10 by means of a shaft seal 152 for preventing leakage of polymer.

A method of producing a laminated tubular body by extrusion molding using the above-described extrusion die according to the present invention will be described below. In the following drawings, the same reference numerals as those in FIG. 2 denote the same or corresponding parts, and the overlapped description of the parts are omitted.

FIG. 3 is a typical view of an extrusion molding line using the above-described rotary point type die 1 for producing a laminated tubular body according to the present invention. The following description will be made mainly by example of producing a three-layer laminated tube made from a thermoplastic material.

Molding devices other than the die 1 may be those commercially available. If needed, components such as a cylinder and a screw of an extruder may be suitably modified within the scope of the production method of the present invention. For example, the components may be each made from a special material such as a corrosion resisting material or a wear resisting material suitable for the production method of the present invention. In addition, the condition and specification of the extruder, such as the size and the plasticization ability of the extruder may be suitably selected depending on requirements for final tubular bodies.

FIG. 3 shows an example in which a three-layer tubular body is produced by using three extruders 2a, 2b, and 2c.

In the case of producing a three-layer laminated tubular body by co-extruding three layers of two kinds of polymers, one layer of one kind of polymer and two layers of the other kind of polymer may be supplied by three extruders, respectively. In this case, the co-extrusion of three layers of two kinds of polymers may be performed by using two extruders. To be more specific, if the inner and outer layers are made from the same polymer, the inner and outer layers of one kind of polymer may be supplied by one extruder, and the intermediate layer of the other kind of polymer be supplied by the other extruder.

Even in the case of forming inner and outer layers by using the same polymer, it is preferred to use three extruders. In this case, the inner and outer layers of one kind of polymer and the intermediate layer of the other kind of polymer may be supplied by the three extruders, respectively. Such use of the three extruders is advantageous in easily adjusting the thickness of each of the inner and outer layers into a specific value by distributing specific amounts of polymers for the inner and outer layers.

Materials in the extruders 2a to 2c are pressed from the polymer inlets 101a to 101c to the die 1 via adapters 21a to 21c, respectively. Gear pumps 22a to 22c are preferably provided if the dimensional accuracy of the final product is required, although they are not necessarily provided.

The proximal end of the shaft 112 of the mandrel 11 of the die 1 is connected to the drive portion 3.

As shown in FIG. 2, thee-layered polymers pressed in the die 1 are shaped into a laminated tubular shape in the die 1, and continuously extruded from the die 1. As shown in FIG. 3, a laminated tubular body 4 extruded from the mouthpiece 151 is solidified in a solidifying bath 5 and is continuously drawn by a drawing machine 6. The dimension of the laminated tubular body 4 is measured by a laser outer-diameter measuring device 61, and thereafter, the laminated tubular body 4 is accumulated by using a winder or cutter 62.

The type of the solidifying bath 5 differs depending on whether the material of the laminated tubular body formed by extrusion molding is a thermoplastic polymer, a polymer solution using a solvent, or a thermosetting polymer, but is generally of a type of solidification by cooling or heating or by using a chemical agent.

If the laminated tubular body is made from a thermoplastic polymer, since the polymer is generally solidified by water-cooling, the solidifying bath 5 is configured as a water bath. In the case of using the water bath, to improve the roundness of the laminated tubular body, an auxiliary device such as a low pressure sizing device or a vacuum water bath may be used, although such a device is not necessarily provided. In particular, the use of the low pressure sizing device is preferable.

In the case of forming a tubular body by extrusion molding, a solid core such as a copper wire, or a mass of liquid or gas may be used as a core material 7.

The use of the solid core material 7 is effective to easily keep the inner diameter of a soft and deformable polymer immediately after being extruded from the mouthpiece 151 into a specific shape; however, from the viewpoints of reducing the cost and eliminating the labor of removing the solid core material, a mass of air or nitrogen gas is often used as the core material 7.

The method of supplying the core material, the method of connecting and arranging the drive portion 3, and the method of transmitting rotation of the drive portion 3 to the rotary point 111 can be suitably selected depending on the kind of core material and the like.

For example, the method of transmitting rotation of the drive portion 3 to the rotary point 111 differs depending on the kind of core material, but is generally represented by a direct coupling method or offset coupling method.

By molding a composite material containing a specific amount of specific reinforcing short-fibers according to the present invention into a tubular parison while adjusting conditions of the molding method as described below and molding the tubular parison into a balloon by a biaxial orientation blow molding process, the short-fibers can be oriented in the following directions specified according to the present invention.

In the case of adopting the above-described rotary extrusion molding process, a balloon material is extruded into a tubular parison (preform) while at least most of the short-fibers undergo external forces in the rotational direction and the major-axis direction. The parison thus obtained is then molded into a balloon by a biaxial orientation blow molding process. In such a balloon, the short-fibers are oriented such that in the longitudinal cross-section of the balloon, 25% or more of the short-fibers are oriented in the major-axis direction, 40% or more of the short-fibers are oriented in the direction oblique to the major-axis direction, and the remaining short-fibers are oriented in the direction nearly perpendicular to the major-axis direction; and in the diametrical cross-section, 15% or more of the short-fibers are oriented in the circumferential direction, 25% or more of the short-fibers are oriented in the direction perpendicular to the circumferential direction, that is, in the major-axis direction, and the remaining short-fibers are oriented in the direction oblique to the circumferential direction.

On the other hand, in the case of adopting the general-extrusion molding process, the short-fibers are oriented in the balloon such that in the longitudinal cross-section of the balloon, 45% or more of the short-fibers are oriented in the major-axis direction, 25% or more of the short-fibers are oriented in the direction oblique to the major-axis direction, and the remaining short-fibers are oriented in the direction nearly perpendicular to the major-axis direction; and in the diametrical cross-section, 8% or more of the short-fibers are oriented in the circumferential direction, 45% or more of the short-fibers are oriented in the direction perpendicular to the circumferential direction, that is, in the major-axis direction, and the remaining short-fibers are oriented in the direction oblique to the circumferential direction.

<Formation of Balloon from the Tubular Parison by Direct Molding>

On the other hand, in the case of using a thermosetting resin or a solution molding type resin as the matrix resin, the balloon 1 of the present invention can be produced by using a balloon molding machine 9 shown in FIG. 4, which machine is one example of the biaxial orientation blow molding machine.

The balloon molding machine 9 includes an inner core 901 and a rotational shaft body 902. The inner core 901 has a shape corresponding to that of the balloon 1 to be produced. The outer surface of the inner core 901 is coated with a liquid composite material 903 composed of the short-fibers 2 and the matrix resin 3, followed by solidification of the composite material, to form the balloon 1. The rotational shaft body 902 is provided so as to be coaxial with the inner core 901 and to pass through the inner core 901.

The inner core 901 must be removed from the balloon 1 without damaging the molded balloon 1. For this reason, the inner core 901 may be made from a water-soluble polymer (for example, polyvinyl alcohol resin), or a polymer removable by melting at a temperature as low as not to damage the molded balloon 1 (for example, ethylene-vinyl acetate (EVA) copolymer, polyethylene, or polypropylene). In particular, the water-soluble polymer is preferable.

In the case of producing the balloon 1 by using the balloon molding machine 9, the outer surface of the inner core 901 is coated with a thermosetting resin or a solution molding type resin containing a necessary amount of reinforcing short-fibers 801. In the case of using polyimide as the solution molding type resin, if polyamic acid is used as a precursor (resin solution), cyclization reaction is required to cause imide rings, and accordingly, the inner core 901 coated with the liquid resin is dipped in anhydrous acetic aid containing a cyclization assistant such as pyridine for a specific time.

After that, as shown in FIG. 4, the balloon molding machine 9 is kept in such a manner that the major-axis (center axis) of the inner core 901 is aligned with the direction of gravity, and the rotational shaft body 902 is rotated in the circumferential direction around the major-axis (center axis) of the inner core 901. As a result, the short-fibers 801 in the liquid resin coated on the inner core 901 are oriented in the major-axis direction of the balloon by the effect of gravity and also oriented in the circumferential direction of the balloon by the effect of a rotational force of the rotational shaft body 902. The rotational speed and the rotational time of the rotational shaft body 902 may be suitably set so that the short-fibers 801 are sufficiently oriented in the specific directions.

The configuration of orienting the short-fibers 801 in the major-axis direction of the balloon by the effect of gravity may be replaced as follows: namely, after the short-fibers 801 are oriented in the circumferential direction of the balloon by rotating the inner core 901 in the circumferential direction as described above, the short-fibers 801 may be oriented in the major-axis direction of the balloon by rotating the inner core 901 around the axial line perpendicular to the above-described major-axis direction.

After the short-fibers 801 are oriented in the specific directions, the liquid resin coated on the outer surface of the inner core 901 is solidified, to form the balloon 1 on the inner core 901. After that, the inner core 901 is removed from the balloon 1, to obtain the balloon 1. If the inner core 901 is made from a water-soluble polymer, the inner core 901 can be removed from the balloon 1 by rinsing.

The present invention will become more apparent by way of the following examples, although the present invention is not limited thereto.

EXAMPLE 1

<Preparation of Fiber-blended Polyamide Elastomer Resin>

Using a biaxial kneader, carbon short-fibers (diameter: 7 μm, average length: 6 mm, aspect ratio: about 850) previously surface-treated by a titanium coupling agent and a polyamide elastomer resin (commercially available from EMS Japan Co., Ltd. in the trade name of Grilamid) are extruded and hot-cut at 220° C., to prepare kneaded pellets. The content of the carbon short-fibers is set to 18 wt % on the basis of the total amount of the polyamide elastomer. The lengths of the short-fibers become short by kneading (compounding), with a result that the average length of the carbon short-fibers in the matrix resin is in a range of 400 to 500 μm and the aspect ratio of each of the carbon short-fibers is in a range of 60 or more.

<Extruding Molding into Tubular Parison of Three-Layer Tube>

Outer and inner layers each of which is made from a polyamide elastomer resin and an intermediate layer made from the above-described fiber-blended polyamide elastomer resin are extruded into a tubular parison by the rotary extrusion molding machine (having the three extruders) shown in FIG. 2. To be more specific, the polyamide elastomer resin for the outer and inner layers is charged in the two extruders and the fiber-blended polyamide elastomer resin for the intermediate layer is charged in the remaining one extruder, and are pressed in the rotary die of the present invention, to form a tubular body (parison) having an inner diameter of 0.5 mm and an outer diameter of 1.0 mm. At this time, the molding temperature is set to 200° C.±5° C., and the temperatures of the extruders and the rotary die are adjusted so as to keep the molding temperature of 200° C.±5° C. The thickness of the outer layer is set to 0.1 mm, the thickness of the intermediate layer is set to 0.05 mm, and the thickness of the inner layer is set to 0.1 mm. The tube drawing speed is set to 12 m/min, and the rotational speed of the rotary point upon extrusion is set to 100 rpm.

A tubular parison having the very smooth three-layer structure is thus obtained.

<Molding into Balloon>

The laminated parison is molded into a balloon (outer diameter: 3.0 mm) by a known biaxial orientation blow molding process using a balloon molding die, and the balloon is assembled into a PTCA balloon catheter by a known method.

COMPARATIVE EXAMPLE 1

For comparison, the procedure in Example 1 is repeated except that a polyamide elastomer resin containing no carbon short-fibers is used as the material for forming the intermediate layer, to form a three-layer tube by molding, mold the three-layer tube into a balloon (outer diameter: 3.0 mm), and assemble the balloon into a PTCA balloon catheter.

<Strength to Withstand Pressure and Properties of Balloon>

The strength to withstand pressure of each of the balloons produced in Example 1 and Comparative Example 1 is measured. As a result, the balloon in Comparative Example 1 exhibits a strength to withstand a pressure of 18 atm, whereas the balloon in Example 1 exhibits a strength to withstand a pressure of 23 atm or more. In addition, the flexibility of the balloon in Example 1 is sufficiently kept. It is to be noted that the strength to withstand pressure is determined by the measurement method described hereunder. Such a measurement result shows that the strength to withstand pressure of the balloon is significantly improved by the reinforcing effect of the carbon short-fibers.

EXAMPLE 2

<Preparation of Fiber-Blended Polyimide Resin>

Nanocarbon tubes of a multi-layer type (outer diameter: 7 nm, length: about 80 nm) are blended in an amount of 15 wt % to a thermoplastic polyimide (commercially available from Mitsui Toatsu Chemicals, Inc. in the trade name of AURUM). To be more specific, the nanocarbon tubes are added in polyamic acid as a precursor of the polyimide in a solution polymerization step of the a precursor, and after formation of polyimide rings, a resin containing the nanocarbon tubes blended in the polymerization step is taken out.

The nanocarbon tube blended thermoplastic polyimide resin is molded into a tubular parison (wall thickness: 0.025 mm) by a known extrusion molding method. In addition, the drawdown ratio in cross-section between the die and tip upon extrusion molding is set to 8:1.

<Molding into Balloon>

The parison is molded into a balloon (outer diameter: 3.0 mm) by a known biaxial orientation blow molding process using a balloon molding die, and the balloon is assembled into a PTCA balloon catheter by a known method.

COMPARATIVE EXAMPLE 2

For comparison, the procedure in Example 2 is repeated except for use of a thermoplastic polyimide resin containing no nanocarbon tubes, to form a tubular parison by molding, mold the parison into a balloon (outer diameter: 3.0 mm), and assemble the balloon into a PTCA balloon catheter.

<Strength to Withstand Pressure and Properties of Balloon>

The strength to withstand pressure of each of the balloons produced in Example 2 and Comparative Example 2 is measured. As a result, the balloon in Comparative Example 2 exhibits a strength to withstand a pressure of 25 atm, whereas the balloon in Example 2 exhibits a strength to withstand a pressure of 35 atm or more. In addition, the flexibility of the balloon in Example 2 is sufficiently kept. Such a measurement result shows that the strength to withstand pressure of the balloon is significantly improved by the reinforcing effect of the nanocarbon tubes.

EXAMPLE 3

<Preparation of Fiber-Blended Polyurethane Resin>

A polyurethane resin (commercially available from Dainippon Ink and Chemicals, incorporated in the trade name of "Pandex") is dissolved in tetrahydrofuran at a concentration of 20%, and carbon short-fibers (diameter: 7 μm, average length: 6 mm, aspect ratio: about 850) are added in the polyurethane solution. The resultant polyurethane solution containing the carbon short-fibers is slowly stirred at 30° C. and is simultaneously irradiated with ultrasonic waves at a frequency of 38 KHz and a power of 600 W for 60 min by an ultrasonic transducer (commercially available from Ultrasonic Engineering Co., Ltd. in the trade name of "Model CM-121").

<Molding into Tubular Parison>

A metal wire having an outer diameter of 1 mm covered with polytetrafluoroethylene (PTFE) is dipped in the short-fiber blended polyurethane solution having been subjected to the ultrasonic vibration treatment, and is then slowly pulled up and dried for 2 hr at 60° C. Such a step is repeated by several times, and finally the metal wire is pulled out, to obtain a double-layer tube having a thickness of about 300 μm (thickness of PTFE layer: 150 μm) and a length of about 200 mm.

<Molding into Balloon>

The laminated parison is molded into a balloon (outer diameter: 3.0 mm) by a known biaxial orientation blow molding process using a balloon molding die, and the balloon is assembled into a PTCA balloon catheter by a known method.

COMPARATIVE EXAMPLE 3

For comparison, the procedure in Example 3 is repeated except for use of a fiber-blended polyurethane resin having been not subjected to ultrasonic vibration treatment, to form a tubular parison by molding, mold the tubular parison into a balloon (outer diameter: 3.0 mm), and assemble the balloon into a PTCA balloon catheter.

<Strength to Withstand Pressure and Properties of Balloon>

The strength to withstand pressure of each of the balloons produced in Example 3 and Comparative Example 3 is measured. As a result, the balloon in Comparative Example 3 exhibits a strength to withstand a pressure of 18 atm, whereas the balloon in Example 3 exhibits a strength to withstand a pressure of 23 atm or more. In addition, the flexibility of the balloon in Example 3 is sufficiently kept. Such a measurement result shows that the strength to withstand pressure of the balloon is significantly improved by the reinforcing effect of the carbon short-fibers having been subjected to ultrasonic vibration treatment.

EXAMPLE 4

<Preparation of Fiber-Blended Polyamide Elastomer Resin>

Using a biaxial kneader, nanocarbon tubes of a multi-layer type (outer diameter: 7 nm, length: about 80 nm, aspect ratio: about 11) and a polyamide elastomer resin (commercially available from EMS Japan Co., Ltd. in the trade name of Grilamid) are extruded and hot-cut at 220° C., to prepare kneaded (compounded) pellets. The content of the nanocarbon tubes is set to 15 wt % on the basis of the total amount of the polyamide elastomer resin.

<Extrusion Molding into Tubular Parison>

The fiber-blended polyamide elastomer resin is molded into a one-layer tubular parison by the rotary extrusion molding machine shown in FIG. 2. The resin is charged in an extruder and is pressed in the rotary die, to be molded into a tubular body as the parison having an inner diameter of 0.5 mm and an outer diameter of 1.0 mm. At this time, the molding temperature is set to 200° C.±5° C. In addition, the drawdown ratio in cross-section between the die and tip upon extrusion molding is set to 8:1.

<Molding into Balloon>

The parison is molded into a balloon (outer diameter: 3.0 mm, wall thickness: 20 μm) by a biaxial orientation blow molding process using a balloon molding die. The nanocarbon tubes in the balloon are oriented such that in the longitudinal cross-section of the balloon, 33% of the nanocarbon tubes are oriented in the major-axis direction (longitudinal axis direction), 42% of the nanocarbon tubes are oriented in the direction oblique to the major-axis direction, and the remaining nanocarbon tubes are oriented in the direction nearly perpendicular to the major-axis direction; and in the diametrical cross-section, 17% of the nanocarbon tubes are oriented in the circumferential direction, 33% of the nanocarbon tubes are oriented in the direction perpendicular to the circumferential direction, and the remaining nanocarbon tubes are oriented in the direction oblique to the circumferential direction. The balloon is then assembled into a PTCA balloon catheter by a known method.

EXAMPLE 5

The same compound resin as that used in Example 4 is extrusion-molded into a tubular parison. The parison is molded into a balloon (outer diameter: 3.0 mm, wall thickness: 20 μm) by a biaxial orientation blow molding process using a balloon molding die. The nanocarbon tubes in the balloon are oriented such that in the longitudinal cross-section of the balloon, 48% of the nanocarbon tubes are oriented in the major-axis direction, 31% of the nanocarbon tubes are oriented in the direction oblique to the major-axis direction, and the remaining nanocarbon tubes are oriented in the direction nearly perpendicular to the major-axis direction; and in the diametrical cross-section of the balloon, 13% of the nanocarbon tubes are oriented in the direction in the circumferential direction, 48% of the nanocarbon tubes are oriented in the direction perpendicular to the circumferential direction, and the remaining nanocarbon tubes are oriented in the direction oblique to the circumferential direction. The balloon is then assembled into a PTCA balloon catheter by a known method.

EXAMPLE 6

<Preparation of Fiber-Blended Polyamide Elastomer Resin>

Using a biaxial kneader, nanocarbon fibers of a multi-layer type (outer diameter: 150 nm, length: 10–20 μm, aspect ratio: about 100) and a polyamide elastomer resin (commercially available from EMS Japan Co., Ltd. in the trade name of Grilamid) are extruded and hot-cut at 220° C., to prepare kneaded pellets. The content of the nanocarbon fibers is set to 15 wt % on the basis of the total amount of the polyamide elastomer.

<Extrusion Molding into Tubular Parison>

The fiber-blended polyamide elastomer resin is molded into a one-layer tubular parison by the rotational extruding molding machine shown in FIG. 2. To be more specific, the resin is charged in an extruder and is pressed in the rotary die, to be molded into a tubular body as the parison having an inner diameter of 0.5 mm and an outer diameter of 1.0 mm. At this time, the molding temperature is set to 200° C.±5° C. In addition, the drawdown ratio in cross-section between the die and tip upon extrusion molding is set to 8:1.

<Molding into Balloon>

The parison is molded into a balloon (outer diameter: 3.0 mm, wall thickness: 20 μm) by a biaxial orientation blow molding process using a balloon molding die. The nanocarbon fibers in the balloon are oriented such that in the longitudinal cross-section of the balloon, 28% of the nanocarbon fibers are oriented in the major-axis direction, 45% of the nanocarbon fibers are oriented in the direction oblique to the major-axis direction, and the remaining nanocarbon fibers are oriented in the direction nearly perpendicular to the major-axis direction; and in the diametrical cross-section, 19% of the nanocarbon fibers are oriented in the circumferential direction, 28% of the nanocarbon fibers are oriented in the direction perpendicular to the circumferential direction, and the remaining nanocarbon fibers are oriented in the direction oblique to the circumferential direction. The balloon is then assembled into a PTCA balloon catheter by a known method.

EXAMPLE 7

<Preparation of Fiber-Blended Polyimide Resin>

Nanocarbon tubes of a multi-layer type (outer diameter: 7 μm, length: about 80 μm, aspect ratio: about 11) are blended in an amount of 15 wt % to a thermoplastic polyimide (commercially available from Mitsui Toatsu Chemicals, Inc. in the trade name of AURUM). To be more specific, the nanocarbon tubes are added in polyamic acid as a precursor of the polyimide in a solution polymerization step of the precursor, and after formation of polyimide rings, a resin containing the nanocarbon tubes blended in the polymerization step is taken out.

<Extrusion Molding into Tubular Parison>

The nanocarbon tube blended thermoplastic polyimide resin is extrusion-molded into a one-layer tubular parison having an inner diameter of 0.5 mm and an outer diameter of 1.0 mm. In addition, the drawdown ratio in cross-section between the die and tip upon extrusion molding is set to 8:1.

<Molding into Balloon>

The parison is molded into a balloon (outer diameter: 3.0 mm, wall thickness: 20 μm) by a biaxial orientation blow molding process using a balloon molding die. The nanocarbon tubes in the balloon are oriented such that in the longitudinal cross-section of the balloon, 52% of the nanocarbon tubes are oriented in the major-axis direction, 29% of the nanocarbon tubes are oriented in the direction oblique to the major-axis direction, and the remaining nanocarbon tubes are oriented in the direction nearly perpendicular to the major-axis direction; and in the diametrical cross-section, 11% of the nanocarbon tubes are oriented in the circumferential direction, 52% of the nanocarbon tubes are oriented in the direction perpendicular to the circumferential direction, and the remaining nanocarbon tubes are oriented in the direction oblique to the circumferential direction. The balloon is then assembled into a PTCA balloon catheter by a known method.

COMPARATIVE EXAMPLE 4

For comparison, the procedure in Example 7 is repeated except for use of a polyamide elastomer resin (commercially available from EMS Japan Co., Ltd. in the trade name of Grilamid) containing no nanocarbon tubes, to form a tubular parison (inner diameter: 0.5 mm, outer diameter: 1.0 mm) by extrusion molding, mold the parison into a balloon (outer diameter: 3.0 mm, wall thickness: 20 μm), and assemble the balloon into a PTCA balloon catheter.

COMPARATIVE EXAMPLE 5

For comparison, the procedure in Example 7 is repeated except for use of a polyamide elastomer resin (commercially available from EMS Japan Co., Ltd. in the trade name of Grilamid) containing no nanocarbon tubes, to form a tubular parison (inner diameter: 0.3 mm, outer diameter: 1.0 mm) by extrusion molding, mold the parison into a balloon (outer diameter: 3 mm, wall thickness: 35 μm), and assemble the balloon into a PTCA balloon catheter.

<Strength to Withstand Pressure and Trackability>

1. The strength to withstand pressure is determined by supplying a pressure from a nitrogen vessel into the balloon and measuring a burst pressure of the balloon.

2. The trackability of the balloon is determined by allowing the balloon to simulatedly pass through a tube, and measuring the resistance of the balloon. The trackability depends on the wall thickness of the balloon, and therefore, the balloon having a wall thickness of 20 μm in each of Example 7 (and in Examples 4, 5, 6) and Comparative Example 4 is good in trackability, whereas the balloon having a wall thickness of 35 μm in Comparative Example 5 is good in strength to withstand pressure but is poor in trackability.

TABLE 1

|  | balloon size (mm) | wall thickness (μm) | strength to burst pressure (kg/cm²) | trackability |
| --- | --- | --- | --- | --- |
| Example 4 | 3.0 | 20 | 23 | ◯ |
| Example 5 | 3.0 | 20 | 21 | ◯ |
| Example 6 | 3.0 | 20 | 25 | ◯ |
| Example 7 | 3.0 | 20 | 27 | ◯ |
| Comparative Example 4 | 3.0 | 20 | 18 | ◯ |
| Comparative Example 5 | 3.0 | 35 | 23 | X |

While the preferred embodiments of the present invention have been described using specific terms, such description is for illustrative purposes only, and it is to be understood that changes and variations may be made without departing from the spirit or scope of the following claims.

What is claimed is:

1. A balloon catheter comprising:
   an elongated body extending between a proximal end and a distal end, said body internally having at least one lumen; and
   a balloon made from a composite material composed of short-fibers for reinforcement and a matrix resin, said balloon being disposed on the distal side of said elongated body;
   wherein the short-fibers in a lonqitudinal cross-section of the balloon comprise short-fibers oriented in the major-axis direction of the balloon, short-fibers oriented in the direction oblique to the major-axis direction and short-fibers oriented in the direction nearly perpendicular to the major-axis direction, and the short-fibers in a diametrical cross-section of the balloon include short-fibers oriented in the circumferential direction of the balloon, short-fibers oriented in the direction perpendicular to the circumferential direction, that is in a major-axis direction, and short-fibers oriented in the direction oblique to the circumferential direction; and
   wherein said short-fibers are oriented in said balloon in such a manner that in the longitudinal cross-section of said balloon 25% or more of said short-fibers are oriented in the major-axis direction of said balloon, 25% or more of said short-fibers are oriented in the direction oblique to the major-axis direction, and the remaining short-fibers are oriented in the direction nearly perpendicular to the major-axis direction; and in the diametrical cross-section of said balloon, 8% or more of said short-fibers are oriented in the circumferential direction of said balloon, 25% or more of said short-fibers are oriented in the direction perpendicular to the circumferential direction, that is, in the major-axis direction, and the remaining short-fibers are oriented in the direction oblique to the circumferential direction.

2. A balloon catheter according to claim 1, wherein said composite material is a material in which said short-fibers are uniformly dispersed in said matrix resin.

3. A balloon catheter according to claim 1, wherein said short-fibers are subjected to a surface modifying treatment.

4. A balloon catheter according to claim 1, wherein said composite material is a material in which said short-fibers are dispersed in said matrix resin by blending said short-fibers in said matrix resin while applying ultrasonic vibration to said short-fibers and said matrix resin.

5. A balloon catheter according to claim 1, wherein said composite material is obtained by blending said short-fibers in a precursor of said matrix resin before polymerization reaction, or in said precursor being during polymerization and thereby having a viscosity lower than a viscosity of the final polymerized product as said matrix resin.

6. A balloon catheter according to claim 1, wherein said short-fiber is at least one kind selected from a group consisting of organic short-fibers and inorganic short-fibers.

7. A balloon catheter according to claim 6, wherein said organic short-fiber is a polymer short-fiber.

8. A balloon catheter according to claim 6, wherein said inorganic short-fiber is at least one kind selected from a group consisting of carbon short-fibers and metal short-fibers.

9. A balloon catheter according to claim 8, wherein said carbon short-fiber is made from nanocarbon.

10. A balloon catheter according to claim 8, wherein said short-fiber is one kind selected from a group consisting of carbon nanotubes and carbon nanofibers.

11. A balloon catheter according to claim 8, wherein said metal short-fiber is a whisker.

* * * * *